United States Patent
Chan et al.

(10) Patent No.: US 9,835,636 B2
(45) Date of Patent: Dec. 5, 2017

(54) SEROLOGICAL MARKERS FOR DETECTING COLORECTAL CANCER AND THEIR APPLICATION FOR INHIBITING COLORECTAL CANCER CELLS

(71) Applicant: CHANG GUNG UNIVERSITY, Tao-Yuan (TW)

(72) Inventors: Err-Cheng Chan, Tao-Yuan (TW); Kuei-Tien Chen, Tao-Yuan (TW); Jau-Song Yu, Tao-Yuan (TW); Yu-Sun Chang, Tao-Yuan (TW); Jinn-Shiun Chen, Tao-Yuan (TW)

(73) Assignee: CHANG GUNG UNIVERSITY, Tao-Yuan (TW)

( * ) Notice: Subject to any disclaimer, the term of this patent is extended or adjusted under 35 U.S.C. 154(b) by 0 days.

(21) Appl. No.: 13/892,011

(22) Filed: May 10, 2013

(65) Prior Publication Data

US 2013/0236913 A1    Sep. 12, 2013

Related U.S. Application Data

(62) Division of application No. 13/252,976, filed on Oct. 4, 2011, now abandoned.

(51) Int. Cl.
| | |
|---|---|
| G01N 33/53 | (2006.01) |
| G01N 33/92 | (2006.01) |
| G01N 33/574 | (2006.01) |
| C07K 14/47 | (2006.01) |
| C12N 9/14 | (2006.01) |

(52) U.S. Cl.
CPC ....... *G01N 33/92* (2013.01); *G01N 33/57419* (2013.01); *C07K 14/47* (2013.01); *C12N 9/14* (2013.01)

(58) Field of Classification Search
None
See application file for complete search history.

(56) References Cited

U.S. PATENT DOCUMENTS

2006/0019256 A1*   1/2006   Clarke et al. ............... 435/6

FOREIGN PATENT DOCUMENTS

| WO | WO 01/75067 | 10/2001 |
|---|---|---|
| WO | WO 2007/047796 | 4/2007 |

OTHER PUBLICATIONS

Kuo et al Mol Med 12: 41-47, Jan.-Feb. 2011.*
Fan et al Clinic Chim Act 412:887-893, published online Jan. 2011.*
ProteinTech blog, published on line Nov. 2010.*
Yeoh et al World J of Gastro 16:2754-63, Jun. 2010.*
Mesh word search result for STOML2, 2014.*
"The Proteintech Blog", blog.ptblag.com, blog, published online Nov. 11, 2010.
Kuo, Yung-Bin, et al., "Identification of Phospholipid Scramblase 1 as a Biomarker and Determination of its Prognostic Value for Colorectal Cancer", Mol Med, (Accepted for Publication Oct. 4, 2010), pp. 41-47, vol. 17 (1-2),2011.
Han, Chai-Li, et al., An Informatics-assisted Label-free Approach for Personalized Tissue Membrane Proteomics: Case Study on Colorectal Cancer, Molecular & Cellular Proteomics, The American Society for Biochemistry and Molecular Biology, Inc. (2011), pp. 1-15, 10-1074.
Cui, Zhumei, et al. "Stomatin-like Protein 2 is Overexpressed and Related to Cell Growth in Human Endometrial Adenocarcinoma" Oncology Reports, (2007) pp. 829-833, vol. 17.
Cao PhD, Wen-Feng, et al. Prognostic Significance of Stomatin-like Protein 2 Overexperssion in Laryngeal Squamous Cell Carcinoma: Clinical, Histologic, and Immunohistochemistry Analysis with Tissue Microarray, Human Pathology (2007) pp. 747-752, vol. 38.
Fan, Chung-Wei, et al. "Identification of SEC61β and its Autoantibody as Biomarkers for Colorectal Cancer", Clinica Chimica Acta, (2011) pp. 887-893, Vo. 412.
Cao PhD, Wenfeng, Cao, et al., "High-Level SLP-2 Expression and HER-2/neu Protein Expression Are Associated With Decreased Breast Cancer Patient Survival", Anatomic Pathology/SLP-2, HER-2 (2007)pp. 430-436, vol. 128.
Zhang, Liyong, et al., "Stomatin-like Protein 2 is Overexpressed in Cancer and Involved in Regulating Cell Growth and Cell Adhension in Human Esophageal Squamous Cell Carcinoma", Clin Cancer Res. (2006), pp. 1639-1646, vol. 12 (5).

* cited by examiner

*Primary Examiner* — Lei Yao
(74) *Attorney, Agent, or Firm* — Muncy, Geissler, Olds & Lowe, P.C.

(57) ABSTRACT

Embodiments relate to serological markers for detecting the colorectal cancer and applications of the serological markers. A phospholipid scramblase1 (PLSCR1), a stomatin-like protein 2 (STOML2) or a transport protein Sec61β (SEC61β) increases expression in the blood at the earlier stage of the colorectal cancer. Detecting the expression of the PLSCR1, STOML2 or SEC61β protein or an induced autoantibody of each protein in a blood sample is used to diagnose the colorectal cancer. Moreover, the serological marker improves the detection efficiency and the sensitivity in detecting the colorectal cancer and is used to predict the prognosis. The serological markers are applied in preparing a detection device or inhibiting the growth of the colorectal cancer cells.

4 Claims, 15 Drawing Sheets
(2 of 15 Drawing Sheet(s) Filed in Color)

SEQUENCE LISTING

<160> NUMBER OF SEQ ID NOS: 3

<210> SEQ ID NO 1
<211> LENGTH: 318
<212> TYPE: PRT
<213> ORGANISM: Homo sapiens
<220> FEATURE:
<221> NAME/KEY: misc_feature
<223> OTHER INFORMATION: PLSCR1

<400> SEQUENCE: 1

```
Met Asp Lys Gln Asn Ser Gln Met Asn Ala Ser His Pro Glu Thr Asn
1               5                   10                  15

Leu Pro Val Gly Tyr Pro Pro Tyr Pro Pro Thr Ala Phe Gln Gly
            20                  25                  30

Pro Pro Gly Tyr Ser Gly Tyr Pro Gly Pro Gln Val Ser Tyr Pro Pro
            35                  40                  45

Pro Pro Ala Gly His Ser Gly Pro Gly Pro Ala Gly Phe Pro Val Pro
        50                  55                  60

Asn Gln Pro Val Tyr Asn Gln Pro Val Tyr Asn Gln Pro Val Gly Ala
65                  70                  75                  80

Ala Gly Val Pro Trp Met Pro Ala Pro Gln Pro Pro Leu Asn Cys Pro
                85                  90                  95

Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
    130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Cys Pro Cys Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
    210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Trp Thr Gly Ile Leu Arg Glu Ala Phe Thr
            260                 265                 270
```

```
Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
    290                 295                 300

Phe Glu Ser Thr Gly Ser Gln Glu Gln Lys Ser Gly Val Trp
305                 310                 315

<210> SEQ ID NO 2
<211> LENGTH: 96
<212> TYPE: PRT
<213> ORGANISM: Homo sapiens
<220> FEATURE:
<221> NAME/KEY: misc_feature
<223> OTHER INFORMATION: SEC61Beta

<400> SEQUENCE: 2

Met Pro Gly Pro Thr Pro Ser Gly Thr Asn Val Gly Ser Ser Gly Arg
1               5                   10                  15

Ser Pro Ser Lys Ala Val Ala Ala Arg Ala Ala Gly Ser Thr Val Arg
            20                  25                  30

Gln Arg Lys Asn Ala Ser Cys Gly Thr Arg Ser Ala Gly Arg Thr Thr
        35                  40                  45

Ser Ala Gly Thr Gly Gly Met Trp Arg Phe Tyr Thr Glu Asp Ser Pro
    50                  55                  60

Gly Leu Lys Val Gly Pro Val Pro Val Leu Val Met Ser Leu Leu Phe
65                  70                  75                  80

Ile Ala Ser Val Phe Met Leu His Ile Trp Gly Lys Tyr Thr Arg Ser
                85                  90                  95

<210> SEQ ID NO 3
<211> LENGTH: 356
<212> TYPE: PRT
<213> ORGANISM: Homo sapiens
<220> FEATURE:
<221> NAME/KEY: misc_feature
<223> OTHER INFORMATION: STOML2

<400> SEQUENCE: 3

Met Leu Ala Arg Ala Ala Arg Gly Thr Gly Ala Leu Leu Arg Gly
1               5                   10                  15

Ser Leu Leu Ala Ser Gly Arg Ala Pro Arg Arg Ala Ser Ser Gly Leu
            20                  25                  30

Pro Arg Asn Thr Val Val Leu Phe Val Pro Gln Gln Glu Ala Trp Val
        35                  40                  45

Val Glu Arg Met Gly Arg Phe His Arg Ile Leu Glu Pro Gly Leu Asn
    50                  55                  60

Ile Leu Ile Pro Val Leu Asp Arg Ile Arg Tyr Val Gln Ser Leu Lys
65                  70                  75                  80

Glu Ile Val Ile Asn Val Pro Glu Gln Ser Ala Val Thr Leu Asp Asn
                85                  90                  95

Val Thr Leu Gln Ile Asp Gly Val Leu Tyr Leu Arg Ile Met Asp Pro
            100                 105                 110

Tyr Lys Ala Ser Tyr Gly Val Glu Asp Pro Glu Tyr Ala Val Thr Gln
        115                 120                 125

Leu Ala Gln Thr Thr Met Arg Ser Glu Leu Gly Lys Leu Ser Leu Asp
    130                 135                 140

Lys Val Phe Arg Glu Arg Glu Ser Leu Asn Ala Ser Ile Val Asp Ala
145                 150                 155                 160
```

```
Ile Asn Gln Ala Ala Asp Cys Trp Gly Ile Arg Cys Leu Arg Tyr Glu
            165             170             175

Ile Lys Asp Ile His Val Pro Pro Arg Val Lys Glu Ser Met Gln Met
            180             185             190

Gln Val Glu Ala Glu Arg Arg Lys Arg Ala Thr Val Leu Glu Ser Glu
            195             200             205

Gly Thr Arg Glu Ser Ala Ile Asn Val Ala Glu Gly Lys Lys Gln Ala
        210             215             220

Gln Ile Leu Ala Ser Glu Ala Glu Lys Ala Glu Gln Ile Asn Gln Ala
225             230             235             240

Ala Gly Glu Ala Ser Ala Val Leu Ala Lys Ala Lys Ala Lys Ala Glu
            245             250             255

Ala Ile Arg Ile Leu Ala Ala Ala Leu Thr Gln His Asn Gly Asp Ala
            260             265             270

Ala Ala Ser Leu Thr Val Ala Glu Gln Tyr Val Ser Ala Phe Ser Lys
            275             280             285

Leu Ala Lys Asp Ser Asn Thr Ile Leu Leu Pro Ser Asn Pro Gly Asp
        290             295             300

Val Thr Ser Met Val Ala Gln Ala Met Gly Val Tyr Gly Ala Leu Thr
305             310             315             320

Lys Ala Pro Val Pro Gly Thr Pro Asp Ser Leu Ser Ser Gly Ser Ser
            325             330             335

Arg Asp Val Gln Gly Thr Asp Ala Ser Leu Asp Glu Glu Leu Asp Arg
            340             345             350

Val Lys Met Ser
            355
```

SEROLOGICAL MARKERS FOR DETECTING COLORECTAL CANCER AND THEIR APPLICATION FOR INHIBITING COLORECTAL CANCER CELLS

CROSS REFERENCE TO RELATED APPLICATIONS

This application is a Divisional of application Ser. No. 13/252,976, filed on 4 Oct. 2011, now abandoned, for which priority is claimed under 35 U.S.C. §120, the entire contents of which are hereby incorporated by reference.

FIELD OF THE INVENTION

Embodiments relate to serological markers for detecting colorectal cancer and a method for using the serological markers, especially to a serological marker for detecting colorectal cancer and a method for using the serological marker with high sensitivity and specificity. Further, embodiments relate to the capability of colorectal cancer inhibition by neutralizing the function of selected serological markers.

BACKGROUND OF THE INVENTION

Cancers are shown as the major causes of death. Earlier detecting of cancer, inhibiting the development and spread of cancer cells, and even researching a method for preventing cancer cells are major issues focused by researchers and the public.

Colorectal cancer (CRC) has been the third common cancer among all cancers. Every year, there are a million new cases and 500,000 people death due to the colorectal cancer. Researches reveal earlier detection and diagnosis will help to decrease the mortality and morbidity of colorectal cancer.

Screening methods currently available for detecting the colorectal cancer include digital rectal examination, fecal occult blood test (FOBT), sigmoidoscopy, and colonoscopy. Although above-mentioned methods have improved the detection efficiency of the colorectal cancer, however, their diagnostic value as a general screening tool is limited because of poor sensitivity and a high false positive rate (FOBT), costs, risks, and inconvenience (colonoscopy). To overcome these problems, the development of novel biomarkers that can allow for the early detection of CRC is crucial.

The advancement of molecular biology, proteomic and preventive medicine provide more useful information or tools to increase the proceeding of develop a novel detection or therapy for colorectal cancer. A biomarker revealing over-expression in tumor tissues (i.e. a tumor tissue or a tissue biopsy) by using one of above-mentioned methods might not release to the circulation of the blood, show a large amount of expression in the blood, or has a long half-life to be detected. A carcinoembryonic antigen (CEA), a clinically established serological marker, is a marker currently widely used in colorectal cancer detection but is always suggested to be used in estimating the prognosis of CRC patients due to the limited sensitivity and specificity.

Accordingly, using different biotechnological methods to search and develop a biomarker to earlier diagnosis the colorectal cancer and to improve the therapeutic efficiency is very important

SUMMARY OF THE INVENTION

According to one aspect of an embodiment of the invention, a serological marker for detecting a colorectal cancer with high sensitivity and specificity at least comprises a phospholipid scramblase 1 (PLSCR1) protein. The PLCSR1 is highly expressed in colorectal cancer patients. Therefore, the colorectal cancer is easy to be determined the possibility and risk by collecting and assaying the PLSCR1 expression in a blood sample instead of invasive obtaining a biopsy. The PLSCR1 protein is increased in the blood at the earlier stage of the colorectal cancer so that the PLSCR1 protein could be applied in the early detection of the colorectal cancer. In an embodiment, the PLSCR1 protein is combined with other proteins, such as SEC61β or STOML2 protein, that are sensitive and specific with the colorectal cancer to improve the detection efficiency.

According to another aspect of an embodiment of the invention, a method for detecting the colorectal cancer comprises steps of establishing a database, collecting a blood sample, detecting a serological marker in the blood sample and comparing the serological maker expression with the database.

According to yet another aspect of an embodiment of the invention, a detection device comprises a sample container, at least a PLSCR1 protein antibody and a substrate. A blood sample is collected and applied in the detection device to test the expression of a serological marker, which is compared with a database to determine the possibility of the colorectal cancer.

Due to the highly sensitivity and specificity to the colorectal cancer, an antigen of the PLSCR1 is used to as a serological marker in detecting the colorectal cancer, and the PLSCR1 or a recombinant protein of PLSCR1 is applied in a detection device for detecting the colorectal cancer. Otherwise, an antibody neutralizing the function of selected serological marker has capability to inhibiting the cell growth of the colorectal cancer.

The above objects and advantages of the present invention will become more readily apparent to those ordinarily skilled in the art after reviewing the following detailed descriptions and accompanying drawings in which:

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

Figure 5:
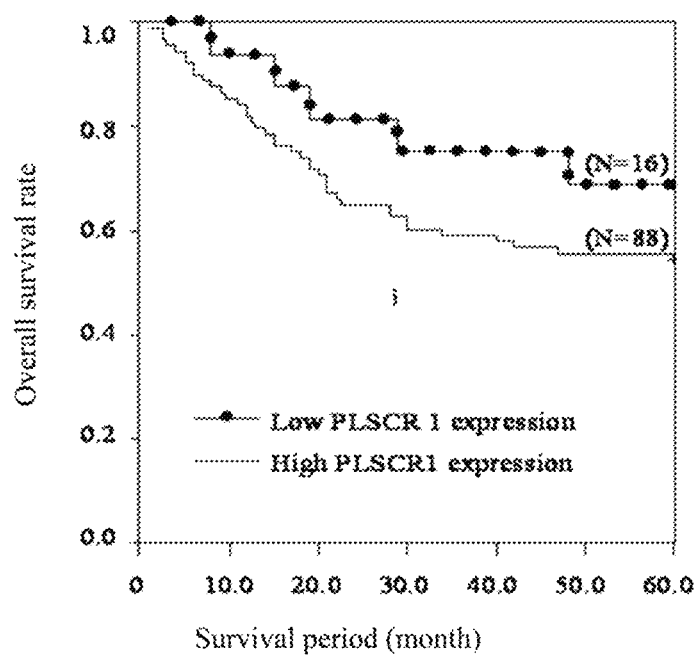
Figure 6:
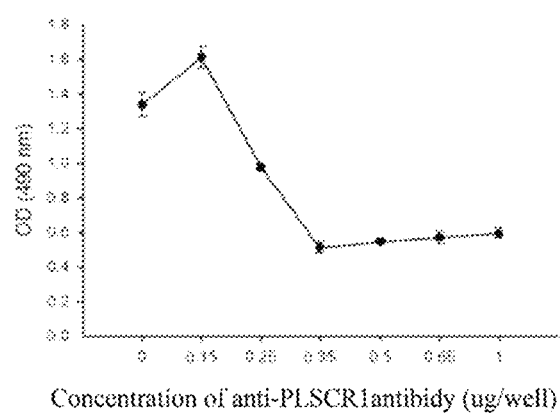
Figure 7:
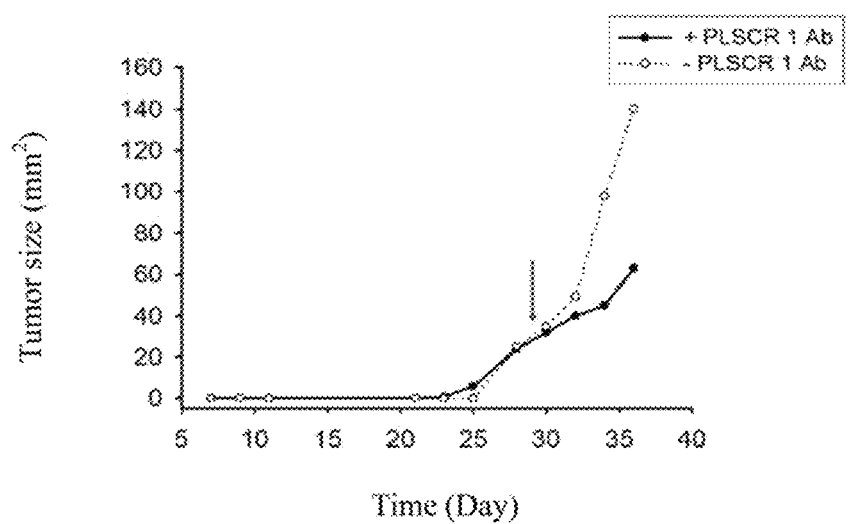
Figure 8:
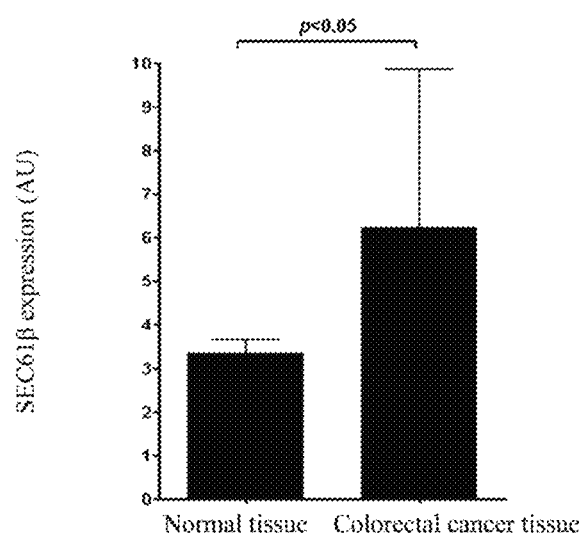
Figure 9:
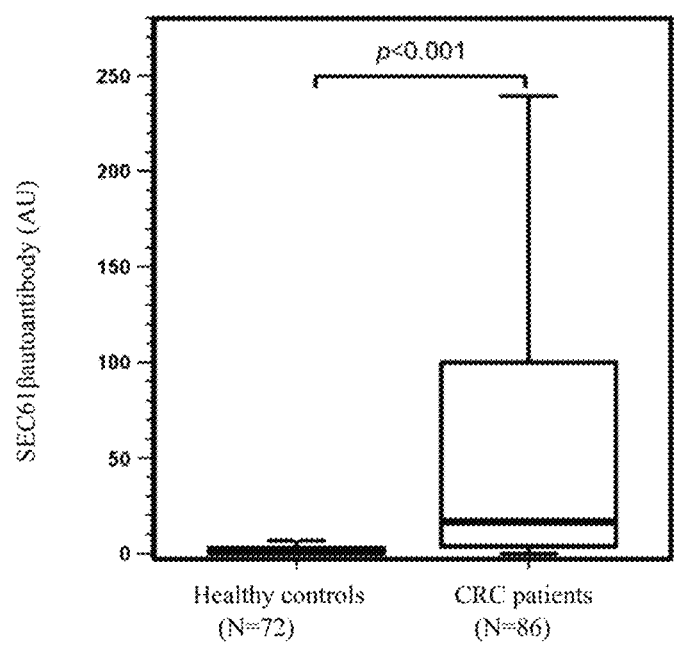
Figure 10:
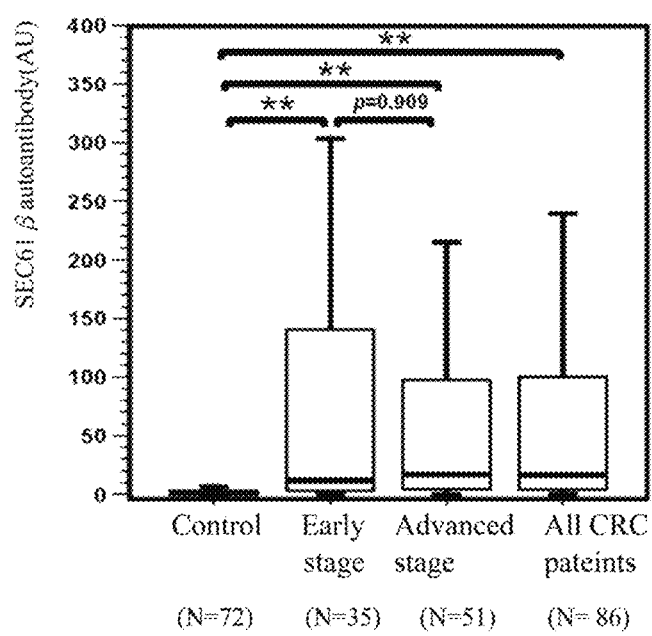
Figure 11:
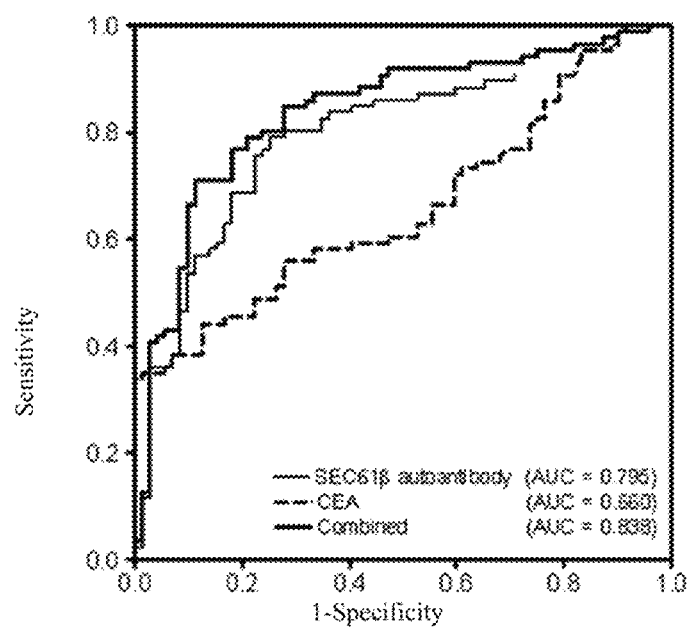
Figure 12:
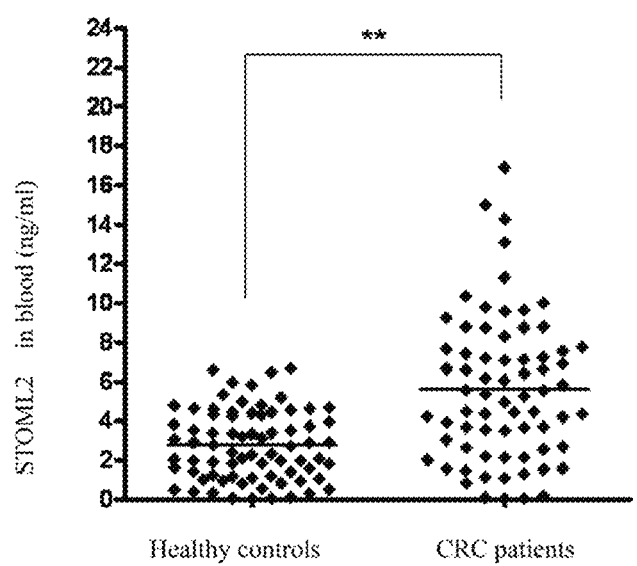
Figure 13:
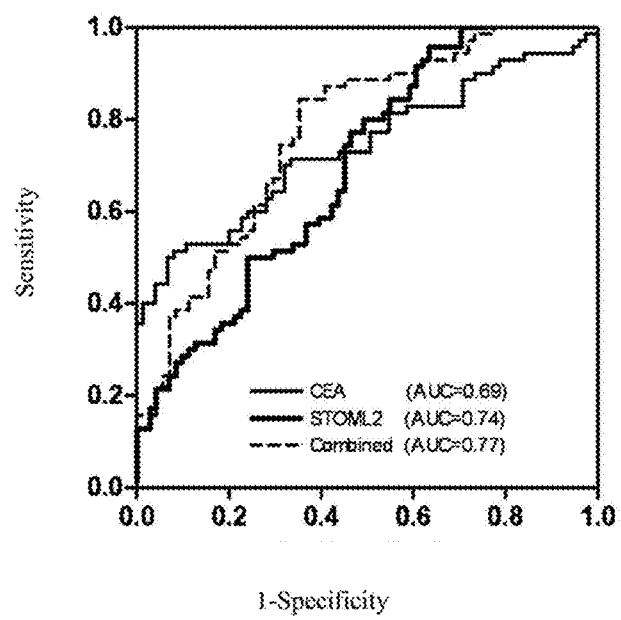
Figure 14:
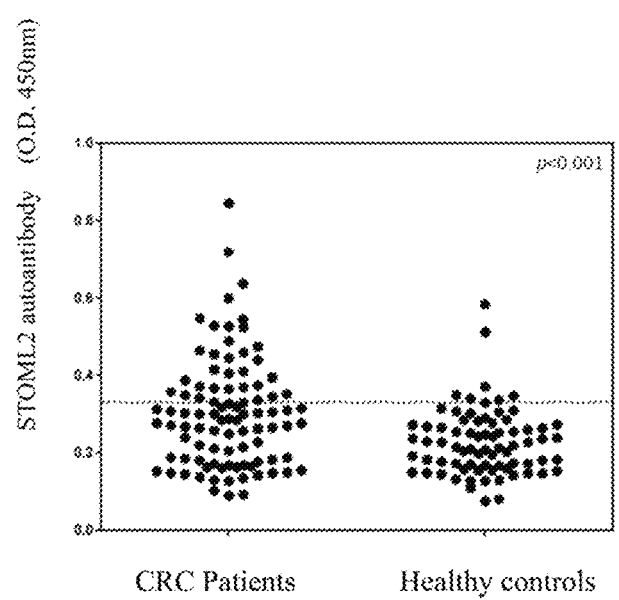
Figure 15:
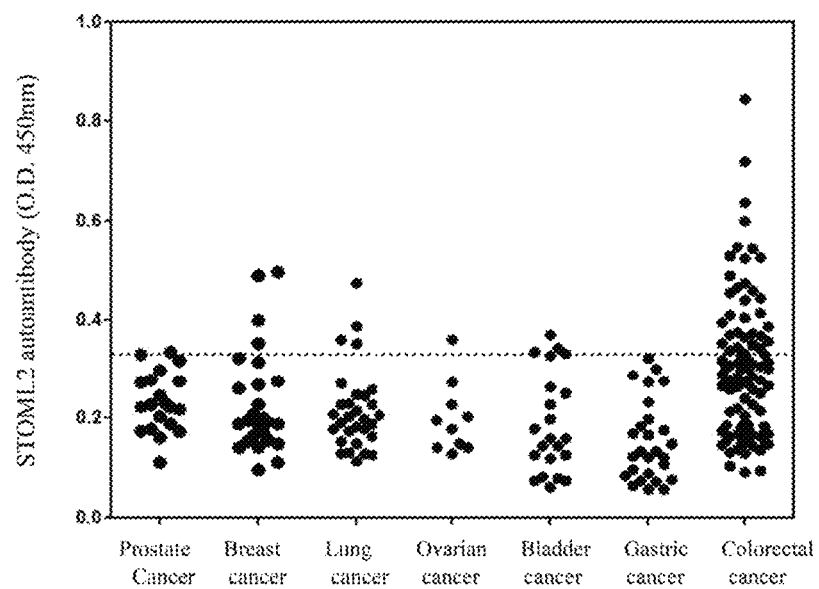

FIG. 5. shows a relationship between the PLSCR1 expression and the overall survival rate of the colorectal cancer patients;

FIG. 6. shows an in vitro inhibition of the colorectal cancer cell growth by treating with a PLSCR1 antibody;

FIG. 7. shows an in vivo inhibition of the colorectal cancer by treating with a PLSCR1 antibody;

FIG. 8. shows the expression of SEC61β protein in the colorectal cancer tissues and the matching normal tissues;

FIG. 9. shows the SEC61β autoantibody response in blood samples of colorectal cancer patients and healthy controls;

FIG. 10. shows the SEC61β autoantibody response at different stages of the colorectal cancer;

FIG. 11. shows the detection efficiency of the SEC61β autoantibody, the current used CEA marker and a combination of both markers;

FIG. 12. shows the expression of STOML2 protein in blood samples of colorectal cancer patients and healthy controls;

FIG. 13. shows the detection efficiency of STOML2 protein, the current used CEA marker and a combination of both markers;

FIG. 14. shows the STOML2 autoantibody response in blood samples of colorectal cancer patients and healthy controls; and FIG. 15. shows the STOML2 autoantibody response in different cancers.

DETAILED DESCRIPTION OF THE PREFERRED EMBODIMENT

Embodiment 1: Screening and Selecting a Serological Marker for Detecting the Colorectal Cancer The embodiment selects a phospholipid scramblase 1 (PLSCR1) as a serological marker for detecting the colorectal cancer. The PLSCR1 is over-expressed in the colorectal cancer tissue and is tested the efficiency as a serological marker to detect the colorectal cancer.

28 colorectal cancer patients are enrolled. A colorectal cancer tissue (tumor tissue) and a normal tissue away from the colorectal cancer tissue for at least 10 centimeters collected from each patient is respectively analyzed the proteomic profile. All tissues are cut into small pieces, washed by using 0.9% sodium chloride to remove blood, homogenized in STM solution (5 ml STM solution/g tissue, 0.25 M sucrose, 10 mM Tris(hydroxymethyl)aminomethane hydrochloride (Tris-HCl) and 1 mM magnesium chloride) to form a homogenous solution.

The homogenous solution is centrifuged at 260×g for 5 minutes to remove the precipitated nuclei and tissue debris. A separated supernatant solution is further centrifuged at 1500×g for 10 minutes to precipitate the crude membrane proteins. The crude membrane proteins are homogenized in two-thirds volume of the original homogenate volume (contains 0.25M STM solution and protease inhibitor) and centrifuged at 16000×g for an hour to purify the membrane proteins. The membrane pellet is washed by 0.1M sodium carbonate for overnight and is centrifuged at 16000×g for an hour to re-collect the membrane proteins. The purified membrane proteins are homogenized in 90% formic acid and stored in −80° C.

The purified membrane proteins are resuspended in 6M urea, 5 mM ethylene diamine tetraacetic acid (EDTA), and 2% sodium dodecyl sulfate (SDS) in 0.1M triethylammonium bicarbonate (TEABC) and sonicated at 4° C. for 10 minutes. A bovine serum albumin (BSA) is used as an internal standard (0.1% BSA in the purified membrane proteins). The purified membrane proteins were reduced by 5 mM Tris(2-carboxyethyl)-phosphine (TCEP) and alkylated by 2 mM methyl methanethiosulfonate (MMTS) at room temperature for 30 mM. A 40% acrylamide solution (acrylamide:bisacrylamide is 29:1, v/v), 10% (w/v) ammonium persulfate (APS) and 100% N,N,N',N'-Tetramethylethylenediamine (TEMED) are added to the purified membrane protein mixture to polymerize as a gel.

The gel is cut into small pieces and subjected to tryptic digestion in 25 mM TEABC solution at 37° C. to form peptides. The peptides are extracted from the gel using sequential extraction with 25 mM TEABC, 0.1% (v/v) trifluoroacetic acid (TFA) in water, 0.1% TFA in acetonitrile (ACN), and 100% ACN. The extracted peptides are concentrated, desalted and analyzed by a liquid chromatography-tandem mass spectrometry (LC-MS/MS).

Information collected from LC-MS/MS is searched by Mascot v2.2 against International Protein Index (IPI) human database from the European Bioinformatics Institute. The selection constraints: (a) only tryptic peptides with up to two missed cleavage sites were allowed; and (b) 0.3-Da mass tolerances for MS and 0.1-Da mass tolerances for MS/MS fragment ions. Only unique peptides with scores ≥35 ($p<0.05$) were confidently assigned. The amino acid sequence of enrolled peptide is further compared to identify the corresponding protein.

Results from the LC-MS/MS analysis are used to compare the expression of a specific protein in the colorectal cancer tissue (tumor tissue) and the normal tissue. For example, peak area of protein A in the colorectal cancer tissue and the normal tissue is R1 and R2 respectively. The peak area of the internal standard in the colorectal cancer tissue and the normal tissue is S1 and S2 respectively. Comparing the ratio of the protein A and the internal standard in the colorectal cancer tissue and the normal tissue, a difference in abundance of 1.5-fold to indicate a statistically significance of higher or lower expression, respectively.

PLSCR 1 is selected from the LC-MS/MS analysis due to the significant overexpression in the colorectal cancer tissue than the matching normal tissue, and is further tested the expression in the western blotting assay and the immunohistochemistry (IHC) assay.

Western Blotting Analysis

The colorectal cancer tissue and the matching normal tissue are suspended in a lysis buffer (0.25 M sucrose, 10 mM Tris-HCl, pH 7.6, 1 mM $MgCl_2$, 1% SDS) with protease inhibitor mixture (20 μg/μL aprotinin, 20 μg/μL leupeptin, and 1 mmol/L phenylmethanesulfonyl fluoride (PMSF); protein:protein inhibitor was 100:1, v/v) and homogenized on ice to form a protein suspension. 40 μg of protein suspension was subjected to the western blot analysis.

With reference to Table 1, Table 1 illustrates the expression of the PLSCR1 in the colorectal cancer tissue compared with their normal counterpart. 18 of 28 paired tissues show at least 1.5 folds overexpression in the colorectal cancer tissue compared with their normal counterpart.

TABLE 1

The expression of the PLSCR1 in the colorectal cancer tissue compared with their normal counterpart.

| No. | Fold (colorectal cancer tissue/normal tissue) |
|---|---|
| 1 | 1.92 |
| 2 | 3.91 |
| 3 | 4.02 |
| 4 | 0.90 |

TABLE 1-continued

The expression of the PLSCR1 in the colorectal cancer tissue compared with their normal counterpart.

| No. | Fold (colorectal cancer tissue/normal tissue) |
|---|---|
| 5 | 1.38 |
| 6 | 0.98 |
| 7 | 4.03 |
| 8 | 2.88 |
| 9 | 2.13 |
| 10 | 3.04 |
| 11 | 0.85 |
| 12 | 2.16 |
| 13 | 1.09 |
| 14 | 3.09 |
| 15 | 12.59 |
| 16 | 11.85 |
| 17 | 10.87 |
| 18 | 2.86 |
| 19 | 6.33 |
| 20 | 1.37 |
| 21 | 2.04 |
| 22 | 2.17 |
| 23 | 1.40 |
| 24 | 0.98 |
| 25 | 8.85 |
| 26 | 0.72 |
| 27 | 6.62 |
| 28 | 5.19 |

The PLSCR1 of the embodiment has an UniProt accession number O15162 with sequence shows as following (SEQ ID NO: 1):

```
         10         20         30         40         50         60
MDKQNSQMNA SHPETNLPVG YPPQYPPTAF QGPPGYSGYP GPQVSYPPPP AGHSGPGPAG 70         80         90        100        110        120
PPVPNQPVYN QPVYNQPVGA AGVPWMPAPQ PPLNCPPGLE YLSQIDQILI HQQIELLEVL 130        140        150        160        170        180
TGPETNNKYE TKNSPGQRVY PAAEDTDCCT RNCCGPSRPF TLRIIDNMGQ EVITLERPLR 190        200        210        220        230        240
CSSCCCPCCL QEIETQAPPG VPIGYVIQTW HPCLPKFTIQ NEKREDVLKI SGPCVVCSCC 250        260        270        280        290        300
GDVDFEIKSL DEQCVVGKIS KHWTGILREA FTDADNFGIQ FPLDLDVKMK AVMIGACFLI

310
DEMFFESTGS QEQKSGVW
```

However, one of ordinary skill in the art will realize that any sequence has more than 90% similarity with above-mentioned sequence is capable to apply in the present invention.

In order to understand whether the PLSCR 1 is significant presented in a blood specimen or has capability to be a serological marker, blood samples respectively from colorectal patients and healthy controls are collected and electrophoresised to separate proteins in blood samples by SDS-PAGE. Proteins in the SDS-PAGE are transferred to a polyvinylidene fluoride (PVDF) membrane. The PVDF membrane is blocked with 5% skim milk in Tris-buffered saline-Tween buffer (25 mmol/L Tris, 190 mmol/L NaCl, and 0.5% [v/v] Tween 20, pH 7.5) and then incubated with primary rabbit antihuman PLSCR1 polyclonal antibody (1:1000 dilution) at 4° C., overnight. After being washed, the membranes were incubated at 25° C. for 1 h with peroxidase-conjugated mouse antirabbit IgG antibody (1:5000 dilution), and then were developed with a chemiluminescence reagent kit and photographed. Immunoblot images were analyzed by an Imagemaster analyser, and the band intensities are presented in arbitrary units (AU).

With reference to FIGS. 1 to 3C, respectively show the PLSCR1 expression in the colorectal tissues and blood samples from CRC patients or healthy volunteers. For the tissue samples, the western blot assay shows the PLSCR1 expression in the colorectal cancer tissue and in the normal tissue is 63.2±41 and 29±28.1 AU ($p<0.001$), respectively. The PLSCR1 expression is at least two folds in the colorectal cancer tissue than in the normal tissue. The IHC assay shows the PLSCR 1 expression increases with the malignant grade of the colorectal cancer in the tissue biopsy. For the blood samples, the western blot assay shows the PLSCR1 is significant expression in the blood samples of the colorectal cancer patients (44 AU) than in the healthy controls (18.5 AU). Therefore, the PLSCR1 has potential to be a serological marker to detect the colorectal cancer.

One of ordinary skill in the art realizes the western blot assay for detecting the PLSCR1 expression might be replaced by an immunoassay such as an enzyme linked immunosorbent assay (ELISA).

One of ordinary skill in the art also obviously understands when the PLSCR1 is highly expressed in the colorectal cancer, a corresponding antibody (autoantibody) induced by the PLSCR1 will be increased. Therefore, the autoantibody of PLSCR1 is able to be a serological marker for detecting the colorectal cancer.

Specificity and Sensitivity of the PLSCR1 for Detecting the Colorectal Cancer

Figure 1:
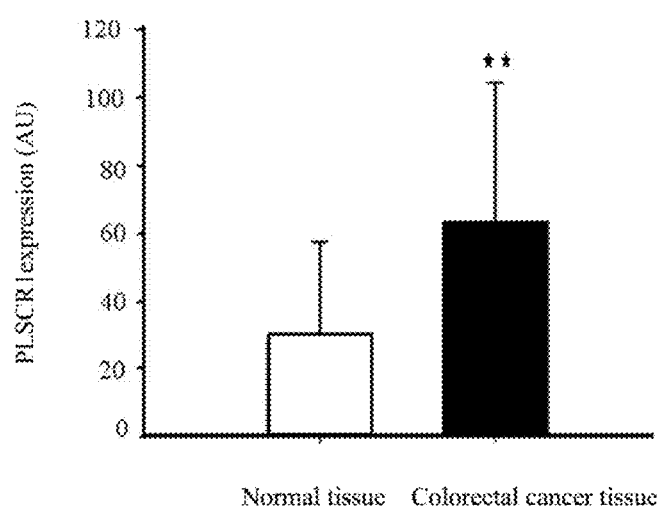
FIG. 1 shows the expression of PLSCR1 protein in colorectal cancer tissues and normal tissues.
Figure 2:
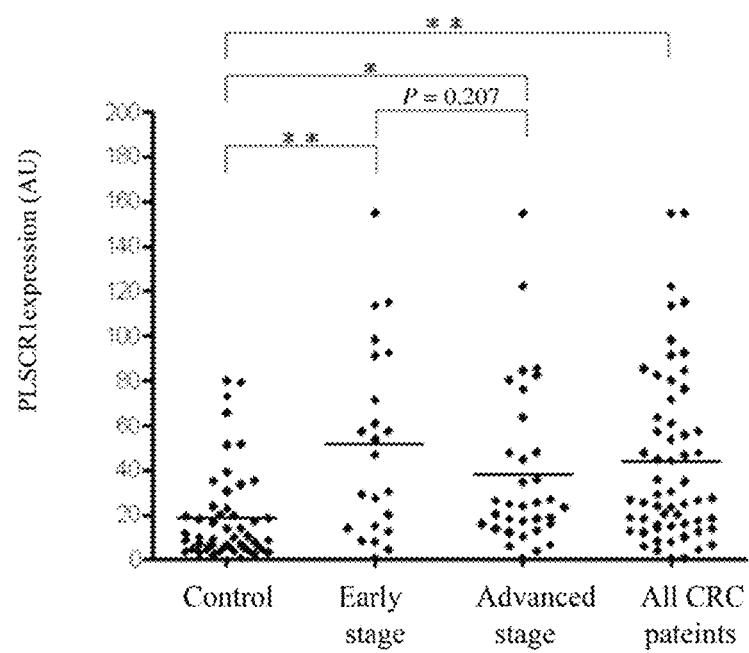
FIG. 2 shows the expression of PLSCR1 protein in blood samples of colorectal cancer patients and healthy controls.
Figure 3A:
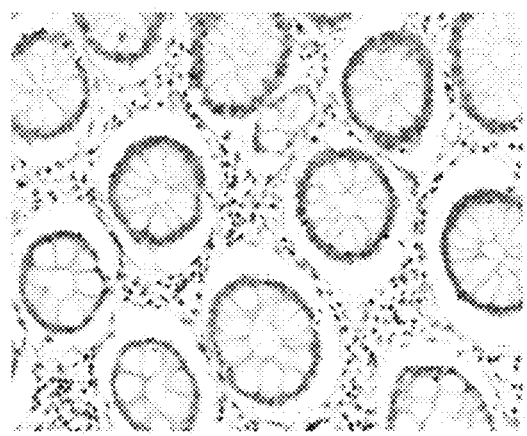
FIG. 3A is a photograph showing the expression of PLSCR1 protein in a normal tissue (normal colorectal mucosa)
Figure 3B:
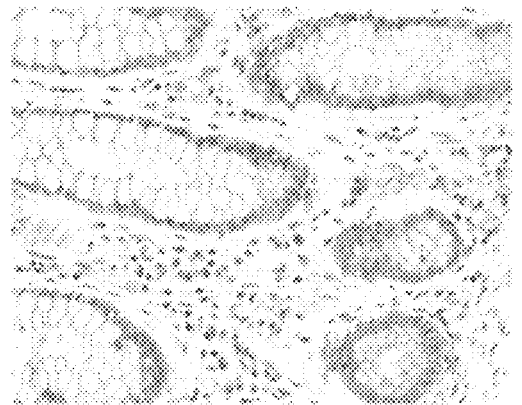
FIG. 3B is a photograph showing the expression of PLSCR1 protein in a benign colorectal polyp tissue.
Figure 3C:
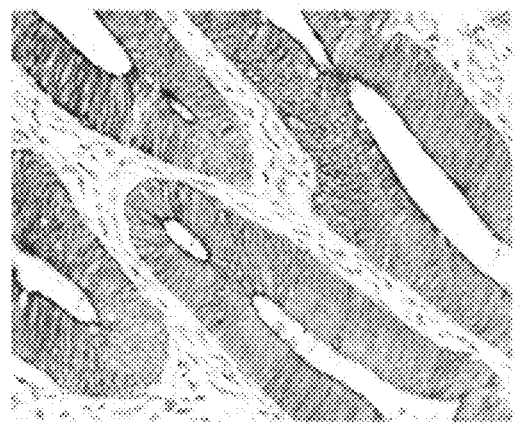
FIG. 3C is a photograph showing the expression of PLSCR1 protein in a colorectal adenocarcinoma tissue.
Figure 4:
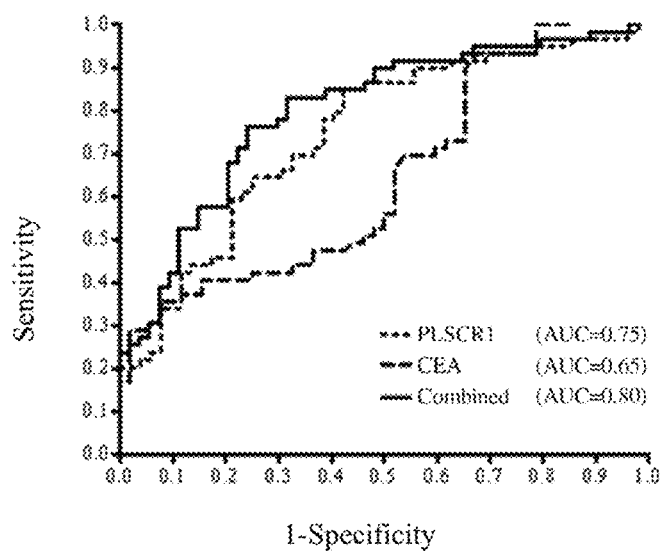
FIG. 4 shows the detection efficiency of PLSCR 1 protein, the current used CEA marker and a combination of both markers.

With reference to FIG. 4 and Table 2, show the comparison between the PLSCR1 and a current used CEA marker.

TABLE 2

Sensitivity of CEA and PLSCR1 in CRC patients with different stage.

| Stage of the colorectal cancer | Numbers of sample | Sensitivity | | |
|---|---|---|---|---|
| | | CEA[a] (A) | PLSCR1[b] (B) | Combined (A) + (B) |
| Early stage | 25 | 4 (16%) | 20 (80%) | 20 (80%) |
| Advanced stage | 34 | 18 (53%) | 27 (79%) | 30 (88%) |
| All CRC patients | 59 | 22 (37%) | 47 (80%) | 50 (85%) |

[a]Cutoff value ≥ 5 ng/mL.
[b]Cutoff value ≥ 13.9 AU.

The PLSCR1 alone has better detection efficiency while applying in detecting the early stage and advanced stage colorectal of cancer than the CEA does. The overall detection rate of the PLSCR1 is at least 2 folds than the CEA so that the PLSCR1 has great capability for detecting the colorectal cancer. Moreover, combination of the PLSCR1 and the CEA will increase the efficiency in CRC detection.

Relationship Between the PLSCR1 Expression and the Overall Survival Rate

With reference to FIG. 5, a Cox proportional hazards model is applied to evaluate the relationship between the PLSCR1 expression and the overall survival rate. The CRC patients were divided into two groups (high PLSCR1 and low PLSCR1) according to a cutoff point of the IHC SI value (SI) by 1. Patients in low PLSCR1 group have longer survival period of 49.8 months than in high PLSCR1 group of 39.2 months. The PLSCR1 expression and the overall survival rate obviously exists a significant relationship.

Further, an anti-PLSCR1 antibody that is produced from the PLSCR1 of the embodiment is used to be identified the capability of CRC inhibition in a mouse model. The anti-PLSCR1 antibody is directly contacted with a colorectal cancer HT29 cells. With reference to FIG. 6, the MTT (3-(4,5-cimethylthiazol-2-yl)-2,5-diphenyl tetrazolium bromide) assay shows the anti-PLSCR1 antibody with concentration more than 0.35 μg/well (μg/mL) is able to inhibit the colorectal cancer cells after two days.

With reference to FIG. 7, after transplanting the HT29 cells ($1\times10^6$ cells) to the subcutaneous region of female nude mice (7 weeks old) for 29 days, respectively injecting an affinity purified anti-PLSCR1 monoclonal antibody (+PLSCR1 Ab) or an IgG (−PLSCR1 Ab) into the mice every two days for 6 days. The anti-PLSCR1 monoclonal antibody significantly inhibits the growth of HT29 cells, but same dose of IgG does not effect the growth of HT29 cells. While observing an H&E staining of the colorectal cancer tissue, the amount of the cancer cells of the colorectal cancer tissue decreases after the mice treated with the anti-PLSCR1 monoclonal antibody. Therefore, the anti-PLSCR1 monoclonal antibody affects and inhibits the cell growth both in vitro and in vivo.

Table 3 shows selected proteins by using the above mentioned methods which might has potential to be colorectal cancer detection markers. The markers are overexpressed in at least 20 tissue pairs from a total of 28 colorectal tissue pairs.

TABLE 3

Proteins have potential to be colorectal cancer detection markers.

| Protein | No. of Patients with Upregulation | Location[a] | Expressed in CRC Tissue[b] | Large Intestine[c] | CRC cell line[c] | | | | | |
|---|---|---|---|---|---|---|---|---|---|---|
| | | | | | COLO 205 | HCT-116 | HCT-15 | HT29 | KM-12 | SW-620 |
| CEACAM5 | 25 | PM | x | x | | | | | x | |
| STOML2 | 24 | PM | | x | x | x | x | x | x | x |
| CEACAM6 | 24 | PM | x | | | | | | | |
| DEFA1 | 24 | Extracellular region | x | | | | | | | |
| RPL36 | 23 | Cytoplasm | | | x | x | x | x | x | x |
| TSPO | 23 | OM | x | x | x | x | x | x | x | x |
| OCIAD2 | 22 | OM | | | x | x | x | x | x | x |
| IKIP | 22 | OM | | | | | | | | |
| CYBA | 22 | PM | | x | x | x | x | x | x | x |
| GOLT1B | 22 | OM | | x | x | x | x | x | x | x |
| ELA2 | 22 | Extracellular region | | | | | | | | |
| CYB5B | 21 | OM | | x | x | x | x | x | x | x |
| SEC61B | 21 | OM | | | x | x | x | x | x | x |
| TOMM40 | 21 | OM | | | x | x | x | x | x | x |
| TMEM63A | 21 | PM | | | x | | x | x | x | x |
| TSPAN8 | 21 | PM | | x | | x | x | x | x | x |
| SLC16A3 | 21 | PM | x | x | x | x | x | x | x | x |
| LAMP1 | 21 | OM | x | | x | | x | x | x | x |
| ANXA4 | 21 | PM | x | x | x | x | x | x | x | x |
| TOMM5 | 21 | Unknown | x | x | x | x | x | x | x | x |
| SLC2A1 | 20 | PM | x | x | x | | x | x | x | x |
| TMCO1 | 20 | OM | | | x | | x | x | x | x |
| OPRS1 | 20 | PM | | x | x | x | x | x | x | x |

[a]the location is annotated by Gene Onotology and Ingenuity Pathway Analysis Knowledge Base. PM indicates plasma membrane and OM indicates organelle membrane
[b]the expression of proteins in colorectal cancer tissues are obtained in Human Protein Reference Database
[c]the data are obtained from Ingenuity Pathway Analysis Accordingly, the PLSCR1 is able to be applied in manufacturing a detection device for detecting the colorectal cancer. The detection device comprises a sample container, at least an anti-PLSCR1 antibody and a substrate. Blood samples are collected and applied in the sample container, and reacts with the anti-PLSCR1 antibody. The substrate might a chromophoric reagent or a fluorescence reagent that is combined with another anti-PLSCR1 antibody and develop a signal related to the binding between the PLSCR1 and the anti-PLSCR1 antibody, which is compared with a database or a cutoff value. The database collects the values of PLSCR1 expression from healthy controls. The cutoff value is calculated by estimating the values of PLSCR1 expression from healthy controls.

Embodiment 2: The Capability of a SEC6β Protein as a Serological Marker for Detecting Colorectal Cancer This embodiment uses a SEC61β protein listed in the Table 3 or an autoantibody induced from the SEC61β protein as a marker to detect the colorectal cancer.

In this embodiment, a comparison of SEC61β expression between the colorectal cancer tissue and the matching normal tissue is established by using western blot assay. Differences between the embodiment 1 and 2 shows as following:

The colorectal cancer tissue and the matching normal tissue is respectively mixed with an electrophoresis buffer contains 2% SDS and 5% 2-mercaptoethanol and heated at 100° C. for 5 minutes. Proteins in the tissues are fractioned by a 12% denatured polyacrylamide gel and then are transferred to the PVDF membrane. The PVDF membrane is blocked with 5% skim milk. Proteins in the PVDF membrane react with a rabbit anti-human SEC61β polyclonal antibody at room temperature for 2 hours and then react with a peroxide-conjugated second antibody at room temperature for 1 hour.

The SEC61β of the embodiment has an UniProt accession number P60468 with sequence shows as following (SEQ ID NO: 2):

```
              10         20         30         40         50         60
    MPGPTPSGTN VGSSGRSPSK AVAARAAGST VRQRKNASCG TRSAGRTTSA GTGGMWRFYT 70         80         90
    EDSPGLKVGP VPVLVMSLLF IASVPMLHIW GKYTPS
```

However, one of ordinary skill in the art will realize that any sequence has more than 90% similarity with above-mentioned sequence is capable to apply in the present invention.

With reference to FIG. 8, the western blot assay indicates that the SEC61β expression in the colorectal cancer tissue is higher than in the normal tissue. A similar result is also shown in an IHC assay.

With reference to FIGS. 9 and 10, shows a relationship between the autoantibody induced from the SEC61β and the colorectal cancer. In the blood samples of colorectal cancer patients, the expression of SEC61β autoantibody is higher than in the blood samples of healthy controls. Also, in the earlier stage of the colorectal cancer, the SEC61β autoantibody in the blood is significantly increased.

With reference to FIG. 11 and Table 4, shows a comparison of the detection efficiency between the SEC60 autoantibody and the current used CEA marker. The SEC61β autoantibody has the sensitivity and the specificity in detection the colorectal cancer by 79% and 75% respectively, whereas for CEA, these values were 40% and 87%, respectively. Combination of the SEC61β autoantibody and the CEA marker show a higher detection capacity than either marker alone (AUC=0.838).

TABLE 4

A comparison of the detection efficiency in the colorectal cancer between the SEC61β autoantibody and the current used CEA marker.

| Sample Source | No. | anti-SEC61βantibody | | | CEA | | | anti-SEC61βantibody + CEA | | |
|---|---|---|---|---|---|---|---|---|---|---|
| | | positive | negative | P value | positive | negative | P value | positive | negative | P value |
| Patient | 86 | 68(79%) | 18(21%) | <0.001 | 34(40%) | 52(60%) | <0.001 | 61(71%) | 25(29%) | <0.001 |
| Healthy volunteer | 72 | 18(25%) | 54(75%) | | 9(13%) | 63(87%) | | 8(11%) | 64(89%) | |

With reference to Table 5, shows the detection efficiency of the SEC6β autoantibody and the current used CEA in detecting CRC patients with different stages. The SEC61β autoantibody has great capability to detect the colorectal cancer in early stage and has detection efficiency more than 75%.

TABLE 5

The detection efficiency of the SEC61β autoantibody and the current used CEA in CRC patients with different stages

| Stage of CRC | Sample No. | CEA positive | SEC61β autoantibody positive | CEA + SEC61β |
|---|---|---|---|---|
| I | 10 | 0(0%) | 8 (80%) | 7(70%) |
| II | 25 | 11(44%) | 19(76%) | 18(72%) |
| I + II | 35 | 11(31%) | 27(77%) | 25(71%) |
| III | 35 | 12(34%) | 29(83%) | 26(74%) |
| IV | 16 | 11(69%) | 12(75%) | 10(63%) |
| III + IV | 51 | 23(45%) | 41(80%) | 36(71%) |
| All | 86 | 34(40%) | 68(79%) | 61(71%) |

This embodiment indicates the SEC61β autoantibody has high capability to be a serological marker to detect the colorectal cancer; especially in the early stage, the SEC61β autoantibody has the detection efficiency more than 75%, which is helpful to promote the early detection and the prognosis evaluation.

Embodiment 3: The Capability of a STOML2 Protein as a Serological Marker for Detecting the Colorectal Cancer A STOML2 protein is selected and listed in the Table 3 to be identified the capability to detect the colorectal cancer.

This embodiment has a difference with the embodiment 2, that is, this embodiment uses an ELISA method to detect the expression of the STOML2 protein in blood samples of colorectal cancer patients or healthy controls.

The STOML2 of the embodiment has an UniProt accession number Q9UJZ1 with sequence shows as following (SEQ ID NO: 3):

```
              10         20         30         40         50         60

MLARAARGTG ALLLRGSLLA SGRAPRRASS GLPRNTVVLF VPQQEAWVVE RMGRFHRILE 70         80         90        100        110        120

PGLNILIPVL DRIRYVQSLK EIVINVPEQS AVTLDNVTLQ IDGVLYLRIM DPYKASYGVE 130        140        150        160        170        180

DPEYAVTQLA QTTMRSELGK LSLDKVFRER ESLNASIVDA INQAADCWGI RCLRYEIKDI 190        200        210        220        230        240

HVPPRVKESM QMQVEAERRK RATVLESEGT RESAINVAEG KKQAQILASE AEKAEQINQA 250        260        270        280        290        300

AGEASAVLAK AKAKAEAIRI LAAALTQHNG DAAASLTVAE QYVSAFSKLA KDSNTILLPS 310        320        330        340        350

NPGDVTSMVA QAMGVYGALT KAPVPGTPDS LSSGSSRDVQ GTDASLDEEL DRVKMS
```

However, one of ordinary skill in the art will realize that any sequence has more than 90% similarity with above-mentioned sequence is capable to apply in the present invention.

With reference to FIGS. 12 and 13, the expression of the STOML2 has significant difference in the blood samples of the colorectal cancer patient and the healthy control, which is similar to the results of the embodiment 1 and 2. Also, combination of the STOML2 protein and the current used CEA marker increases the detection capability of the STOML2 protein.

With reference to FIGS. 14 and 15, shows the detection efficiency and the specificity of the STOML 2 autoantibody in detecting the colorectal cancer. The STOML 2 autoantibody in the blood sample of the colorectal cancer is significantly higher than in the healthy control. The STOML 2 autoantibody level in the colorectal cancer is also higher than other cancers.

Embodiment 4

In this embodiment, the sensitivity and the specificity of different antigens is calculated by a backward elimination method with multivariate logistic regression model. All antigens have excellent specificity and are able to be applied alone or combined each other to improve the efficiency of the colorectal cancer detection.

TABLE 6

The sensitivity and the specificity of different antigens in detecting the colorectal cancer

| antigen | sensitivity (%) | specificity (%) | AUC[1] | p value[2] |
|---|---|---|---|---|
| RPH3AL | 13.83 | 90.67 | 0.554 | 0.33 |
| RPL36 | 22.34 | 96 | 0.597 | <0.05 |
| STOML2 | 36.17 | 90.67 | 0.666 | <0.001 |
| P53 | 31.91 | 94.67 | 0.655 | <0.001 |
| Survivin | 14.89 | 93.33 | 0.574 | 0.07 |
| ANXA4 | 11.7 | 94.67 | 0.523 | 0.51 |
| SEC61β | 18.09 | 97.33 | 0.612 | <0.001 |

TABLE 6-continued

The sensitivity and the specificity of different antigens in detecting the colorectal cancer

| antigen | sensitivity (%) | specificity (%) | AUC[1] | p value[2] |
|---|---|---|---|---|
| STOML2 + P53 + Survivin + ANXA4 | 52.1 | 88 | 0.754 | |

[1]AUC: area under ROC curve
[2]p-value is calculated by t-test

What is claimed is:

1. A method for detecting and treating colorectal cancer, comprising:
   obtaining a blood sample from a human;
   detecting PLSCR1 and STOML2 proteins in said collected blood via an immunoassay selected from the group consisting of Western blot assay and enzyme linked immunosorbent assay (ELISA);
   quantifying protein expression levels of PLSCR1 and STOML2 in said collected blood via liquid chromatography-tandem mass spectrometry (LC-MS/MS);
   comparing the protein expression levels of PLSCR1 and STOML2 with a cutoff value to determine whether said human is at increased risk of having colorectal cancer or not; wherein if the levels are above the cutoff value said human has colorectal cancer, and
   administering anti-PLSCR1 antibody to said human having colorectal cancer.

2. The method as claimed in claim 1, wherein said detecting further includes detecting SEC61β in said collected via the immunoassay.

3. The method as claimed in claim 2, wherein protein expression level of SEC61β is quantified by the immunoassay on SEC61β or an induced autoantibody of SEC61β.

4. The method as claimed in claim 3, wherein said comparing further includes comparing the protein express level of SEC61β with the cutoff value.

* * * * *